United States Patent

Nishioka et al.

Patent Number: 5,702,850
Date of Patent: Dec. 30, 1997

[54] THERMOSENSITIVE REVERSIBLE COLOR-DEVELOPING AND DISAPPEARING AGENT

[75] Inventors: Makoto Nishioka, Ichikawa; Kazuo Yamane; Masaki Nishimura, both of Tokyo; Yoshiyuki Takahashi, Kawasaki, all of Japan

[73] Assignee: New Oji Paper Co., Ltd., Tokyo, Japan

[21] Appl. No.: 527,810

[22] Filed: Sep. 13, 1995

[30] Foreign Application Priority Data

| Sep. 14, 1994 | [JP] | Japan | 6-220189 |
| Feb. 7, 1995 | [JP] | Japan | 7-019184 |
| Feb. 28, 1995 | [JP] | Japan | 7-040401 |

[51] Int. Cl.$^6$ ................ B41M 5/30
[52] U.S. Cl. ........... 430/19; 503/201; 503/216; 430/964; 558/61; 558/234; 558/235; 558/241; 560/13; 560/133; 564/23; 564/42
[58] Field of Search ............ 503/201, 216; 430/19, 342, 964, 332, 338; 564/23, 39, 42; 558/61, 234, 235, 241; 560/13, 133

[56] References Cited

U.S. PATENT DOCUMENTS

| 4,423,116 | 12/1983 | Fox | 428/411 |
| 5,246,906 | 9/1993 | Takahashi et al. | 503/209 |

FOREIGN PATENT DOCUMENTS

| 0492628 | 12/1991 | European Pat. Off. |
| A 0 526 072 A1 | 2/1993 | European Pat. Off. |
| A 0 535 887 A1 | 4/1993 | European Pat. Off. |
| 0574879 | 12/1993 | European Pat. Off. |
| 58-191190A | 11/1983 | Japan |
| 60-193691A | 10/1985 | Japan |
| 60-264285A | 12/1985 | Japan |
| 62-140881A | 6/1987 | Japan |
| 63-173684A | 7/1988 | Japan |
| 2-188293A | 7/1990 | Japan |
| 2-188294A | 7/1990 | Japan |
| 3-233490A | 10/1991 | Japan |
| 5-42762A | 2/1993 | Japan |
| 5-124360 | 5/1993 | Japan |
| 6-210954A | 8/1994 | Japan |
| 93/08161 | 4/1993 | WIPO | 564/39 |

OTHER PUBLICATIONS

Abstract of WO 88/00724, Kuse et al (Jan. 1988).

*Primary Examiner*—John A. McPherson
*Attorney, Agent, or Firm*—Armstrong, Westerman, Hattori, McLeland & Naughton

[57] ABSTRACT

A thermosensitive reversible color-developing and disappearing agent includes an aromatic compound having at least one group of the formula, —$SO_2NHCXNH$—, wherein X=O or S atom, and at least one straight chain alkyl group with 11 or more carbon atoms, and is reactive with a dye precursor in a thermosensitive recording material to thereby record colored images on the recording material upon heating imagewise, and make the colored images disappear upon heating to a temperature lower than the colored image-forming temperature.

7 Claims, 1 Drawing Sheet

THERMOSENSITIVE REVERSIBLE COLOR-DEVELOPING AND DISAPPEARING AGENT

BACKGROUND OF THE INVENTION

1. Field of the Invention

The present invention relates to a thermosensitive reversible color-developing and disappearing (erasing) agent, a thermosensitive reversible colored image-recording and disappearing (erasing) material containing the agent, and a method of reversible recording and making disappear colored images on the material.

More particularly, the present invention relates to a thermosensitive reversible color-developing and disappearing agent which is capable of color-developing and disappearing colored images upon heating, and of maintaining the developed color clear and the disappeared color disappear both at room temperature, the developed color having a high contrast with the disappeared color, and is useful for producing a thermsensitive record material on which colored images can be reversible recorded and made to disappear;

a thermosensitive reversible colored image-recording and disappearing (erasing) material utilizing the agent; and
a method of reversible recording and making disappear (or erasing) colored images on the recording material.

2. Description of the Related Art

Generally, since thermosensitive recording apparatus is compact, cheap and is easy to maintain, thermosensitive recording material has been used in a broad range of applications, for example, outputs of computers, facsimiles, automatic ticket vending machines, prepaid cards and printers for scientific and measurement equipment, printers for medical measurements and the like. However, in the conventional thermosensitive recording materials, since the colored images cannot be made to disappear, the colored image-recorded materials cannot be re-used as a thermosensitive recording material.

Currently, protection of forest and prevention of environmental polution has become very important. In view of the strong demand for environmental protection, the regeneration and re-use of thermosensitive recording sheets are desired. The regeneration and re-use of the thermosensitive recording sheet can be effected by various systems. Among these possible systems, as a wide use-system for various purposes which does not need a large scale apparatus, for example, an apparatus for removing ink, a reversible-type recording system in which colored images can be developed on a recording material upon heating under certain conditions, and if necessary, can be reversible made to disappear upon heating under other conditions, and thus the recording material can be repeatedly used many times, is strongly demanded.

The reversible type thermosensitive recording material now becomes an important recording material not only for thermosensitive recording systems but also for display devices as, for example, disclosed in Japanese Unexamined Patent Publication (Kokai) Nos. 3-233,490 and 5-42,762.

Also, the development of new recording material suitable for the display devices is strongly demanded.

To meet with the above-mentioned demands, there have been made various attempts to produce reversible thermosensitive recording materials.

Reversible thermosensitive recording materials can be briefly classified into two groups, namely polymer-type recording materials in which a change in transparency derived from difference in heating conditions is utilized, and dye-type recording materials in which a change in absorbed wavelength derived from difference in heating conditions is utilized.

The polymer-type reversible thermosensitive recording materials are further classified into polymer mixture type, high molecular material-low molecular material mixture type, and polymer-liquid crystal mixture type. These types of the reversible recording materials basically utilize the change in transparency derived from a change in phase. These polymer-type reversible recording materials are disadvantageous in that it is difficult to obtain satisfactory transparency and opaqueness and the contrast, in color density, between the color-developed portions and the color-disappeared portions.

The dye-type reversible thermosensitive recording materials are materials in which, although dyes usable for the conventional non-reversible thermosensitive recording materials are used, the reversible colored image-recording is made possible. With respect to this type of reversible recording materials, the following attempts have been made.

Japanese Unexamined Patent Publication (Kokai) Nos. 2-188293 and 2-188294 disclose a dye-type reversible recording material in which a salt of a specific organic acid, for example, gallic acid, with a higher aliphatic amine is employed as a color-developing and disappearing agent.

The color-developing and disappearing agent serves as a color-developing agent upon heating to a certain temperature range, and then as a color-subtracting agent upon heating to a higher temperature range than the color-developing temperature range. Therefore, by utilizing the color-developing and subtracting agent, a reversible thermosensitive recording can be effected. However, the color-developing reaction and the color-subtracting reaction are competitive to each other, and thus it is practically difficult to control these reactions so that one of the two reactions selectively advances, and a high contrast in color density cannot be obtained.

Also, Japanese Unexamined Patent Publication (Kokai) Nos. 5-124,360 and 6-210,954 discloses a reversible recording material in which an organic phosphoric acid compound having a long alkyl group, an organic carboxylic acid having a hydroxyl group located in the α-position of the compound, or a phenolic compound, is employed as a color-developing agent. Where this type of reversible recording material is used, the color-disappearing operation is effected by utilizing a phenomenon that when the colored images are heated to the temperature lower than the color-developing temperature, the above-mentioned specific color-developing agent is crystallized and separated from dye so as cause the colored images to disappear. However, in this recording material, the disappearing of the colored images is frequently insufficient and the retention of the colored images is often unsatisfactory.

Further, Japanese Unexamined Patent Publication (Kokai) No. 63-173,684 discloses a reversible recording material using, as a color-developing agent, an ascorbic acid-6-acyl derivative. This recording material is disadvantageous in that the elimination of the colored images is insufficient and a high contrast between the colored portions and color-disappeared portions cannot be obtained.

Furthermore, Japanese Unexamined Patent Publication (Kokai) Nos. 60-264,285 and 62-14,088 disclose a reversible recording material in which an additive consisting of an organic acid ester having a differential temperature ΔT of 5° to 50° C. between the melting temperature and the clouding temperature is employed in addition to the dye and the color-developing agent. In this type of reversible recording material, the colored-images are developed upon cooling to a temperature lower than room temperature, and are made to disappear upon heating to a temperature higher than room temperature. Also, the colored images are maintained at room temperature and the disappeared color images are maintained at room temperature. This type of reversible system is disadvantageous in that since the range of temperature in which the colored images are maintained appear is limited both at the upper end and the lower end thereof, the recording apparatus becomes complicated and the system can be practically employed only in a limited circumstance.

Still furthermore, Japanese Unexamined Patent Publication (Kokai) Nos. 58-191,190 and 60-193,691 disclose a reversible recording material using, as a color-developing agent, gallic acid and phloroglucinol. In this recording material, the color-development is effected upon heating, and the colored images are made to disappear by bringing the colored images into contact with water or water vapor. This type of recording material is disadvantageous in that the durability of the colored images in storage is insufficient and the color-disappearing apparatus must be large.

As explained above, many attempts have been made to provide thermosensitive reversible color-developing and disappearing recording or display materials. They are still unsatisfactory due to the above-mentioned disadvantages. No satisfactory thermosensitive reversible color-developing and disappearing record material has been provided.

SUMMARY OF THE INVENTION

Figure 1:
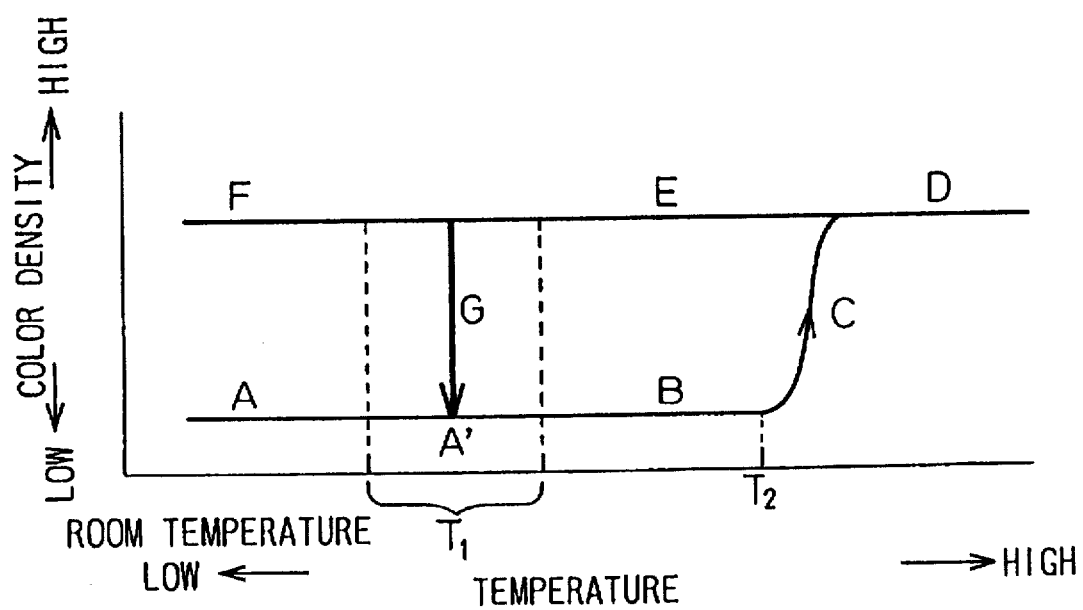
FIG. 1 is a graph showing a relationship between temperature and color density of colored images in the reversible color-developing and disappearing procedures in accordance with the method of the present invention.

An object of the present invention is to solve the above-mentioned problems of the prior arts and to provide a thermosensitive reversible color-developing and disappearing agent, the color-development and disappearing being effected only by heating, the contrast between the color density of developed color and the color density after the color is made to disappear, is high, a thermosensitive reversible colored image-recording and disappearing material containing the color-developing and disappearing agent and capable of reversible forming and disappearing colored images thereon, and a method of reversible forming and making disappear colored images on the material.

The inventors of the present invention have made an extensive research focused on a dye-type thermosensitive reversible colored image-recording or displaying and disappearing system in which a reaction between a dye and a color-developing agent is utilized, to provide a thermosensitive recording material capable of reversible forming and disappearing colored images thereon only by heating and exhibiting a high contrast between the developed color density and the disappeared color density. As a result of the research, it was found that the target thermosensitive reversible colored image-recording and disappearing material can be obtained by using, as a color developing agent, a non-phenolic urea-derivative having a long chain alkyl group.

The present invention was completed on the basis of this finding.

The thermosensitive reversible color-developing and disappearing agent of the present invention for a colored image-recording material, comprises at least one color-developing aromatic compound having, per molecule thereof, at least one sulfonyl(thio)urea group of the formula (I):

wherein X represents a member selected from the class consisting of oxygen and sulfur atoms, and at least one straight chain alkyl group having 11 or more carbon atoms, the color-developing aromatic compound being reactive with a substantially colorless dye precursor of the recording material to thereby develop a color upon heating and make the color disappear upon heating to a temperature lower than the color-developing temperature. In the thermosensitive reversible color-developing and disappearing agent as mentioned above, the color-developing aromatic compound is preferably selected from the class consisting of the compounds the formulae (II) and (III):

and

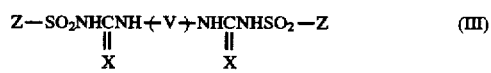

wherein X is as defined above, Y represents a member selected from the class consisting of unsubstituted aromatic cyclic groups, and substituted aromatic cyclic groups with at least one substituent selected from the class consisting of lower alkyl groups, halogen atoms and lower alkoxyl groups; Z represents a member selected from the class consisting of (1) straight chain alkyl groups having 11 or more carbon atoms, (2) aromatic cyclic groups substituted with at least one straight chain alkyl group having 11 or more carbon atoms, (3) aralkyl groups of which the aryl group is substituted with at least one straight chain alkyl group having 11 or more carbon atoms, and (4) aromatic groups each consisting of an aromatic cyclic group and at least one straight chain alkyl group having 11 or more carbon atoms and attached to the aromatic cyclic group through a divalent organic group, in the group represented by Z, each of the aromatic cyclic group (2), the aryl group of the aralkyl group (3), and the aromatic cyclic group of the aromatic group (4) may be further substituted with at least one additional substituent selected from the class consisting of lower alkyl groups, aryl groups, halogen atoms and lower alkoxy groups, and V represents a divalent organic group.

The thermosensitive reversible colored image-recording and disappearing material of the present invention comprises a substrate sheet and a thermosensitive colored image forming layer formed on the substrate sheet and comprising a substantially colorless dye precursor and a reversible color-developing and disappearing agent reactive with the dye precursor to thereby develop a color upon heating and disappear the color upon heating to a temperature lower than the color-developing temperature, and a binder, the color developing agent comprising at least one color-developing aromatic compound having, per molecule thereof, at least one sulfonyl(thio)urea group of the formula (I):

wherein X represents a member selected from the class consisting of oxygen and sulfur atoms, and at least one straight chain alkyl group having 11 or more carbon atoms.

In the thermosensitive reversible colored image-recording and disappearing material as mentioned above, the color-developing aromatic compound is preferably selected from the class consisting of the compounds of the formulae (II) and (III):

    (II)

and

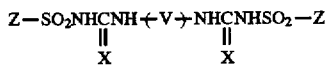    (III)

wherein X is as defined above, Y represents a member selected from the class consisting of unsubstituted aromatic cyclic groups, and substituted aromatic cyclic groups with at least one substituent selected from the class consisting of lower alkyl groups, halogen atoms and lower alkoxyl groups; Z represents a member selected from the class consisting of (1) straight chain alkyl groups having 11 or more carbon atoms, (2) aromatic cyclic groups substituted with at least one straight chain alkyl group having 11 or more carbon atoms, (3) aralkyl groups of which the aryl group is substituted with at least one straight chain alkyl group having 11 or more carbon atoms, and (4) aromatic groups each consisting of an aromatic cyclic group and at least one straight chain alkyl group having 11 or more carbon atoms and attached to the aromatic cyclic group through a divalent organic group, in the group represented by Z, each of the aromatic cyclic group (2), the aryl group of the aralkyl group (3), and the aromatic cyclic group of the aromatic group (4) may be further substituted with at least one additional substituent selected from the class consisting of lower alkyl groups, aryl groups, halogen atoms and lower alkoxyl groups, and V represents a divalent organic group.

The method of the present invention for reversible recording and making disappear colored images on the thermosensitive reversible colored image-forming and disappearing record or display material as mentioned above comprises the repeated steps of: heating imagewise the thermosensitive colored image-forming layer to record colored images on the colored image-forming layer; and after the recorded colored images become unnecessary, reheating the colored image-recorded layer to a temperature lower than the colored image-forming temperature and sufficient to make the colored images disappear.

DESCRIPTION OF THE PREFERRED EMBODIMENTS

In the present invention, the thermosensitive reversible color-developing and disappearing aromatic compound has, per molecule thereof, (1) at least one sulfonyl(thio)urea group of the formula (I):

    (I)

wherein X represents a member selected from the class consisting of oxygen and sulfur atoms, and (2) at least one straight chain alkyl group having 11 or more carbon atoms, preferably 11 to 30 carbon atoms, still more preferably 14 to 21 carbon atoms. The aromatic compound of the present invention is reactive with a substantially colorless dye precursor of the recording material to thereby develop a color upon heating and make the color disappear upon heating to a temperature lower than the color-developing temperature.

The color-developing aromatic compound usable for the present invention is preferably selected from the class consisting of those having the formulae (II) and (III):

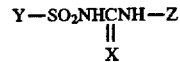    (II)

and

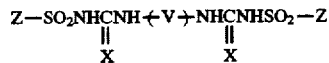    (III)

In the formulae (II) and (III), X is as defined above, Y represents a member selected from the class consisting of unsubstituted aromatic cyclic groups, and substituted aromatic cyclic groups with at least one substituent selected from the class consisting of lower alkyl groups, more preferably having 1 to 8 carbon atoms, halogen atoms, more preferably chlorine and bromine atoms, and lower alkoxyl groups more preferably having 1 to 8 carbon atoms; Z represents a member selected from the class consisting of (1) straight chain alkyl groups having 11 or more carbon atoms more preferably 11 to 30 carbon atoms, (2) aromatic cyclic groups substituted with at least one straight chain alkyl group having 11 or more carbon atoms more preferably 11 to 30 carbon atoms, (3) aralkyl groups of which the aryl group is substituted with at least one straight chain alkyl group having 11 or more carbon atoms more preferably 11 to 30 carbon atoms, and (4) aromatic groups each consisting of an aromatic cyclic group and at least one straight chain alkyl group having 11 or more carbon atoms more preferably 11 to 30 carbon atoms, and attached to the aromatic cyclic group through a divalent organic group. In the groups represented by Z, each of the aromatic cyclic group (2), the aryl group of the aralkyl group (3), and the aromatic cyclic group of the aromatic group (4) may be further substituted with at least one additional substituent selected from the class consisting of lower alkyl groups more preferably having 1 to 8 carbon atoms, aryl groups for example, phenyl and tolyl groups, halogen atoms more preferably chlorine and bromine atoms and lower alkoxyl groups more preferably having 1 to 8 carbon atoms. Also, in the formulae (II) and (III), V represents a divalent organic group.

In the color-developing aromatic compounds of the formula (II), the groups represented by Y are preferably selected from:

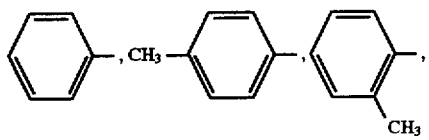

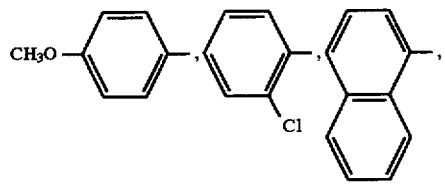

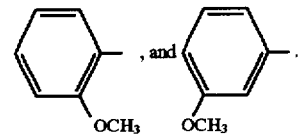

In the color-developing aromatic compounds of the formulae (II) and (III), the groups represented by Z are preferably selected from those of the formulae:
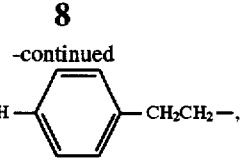
-continued
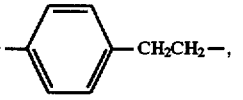
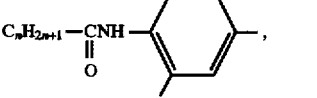
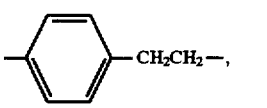
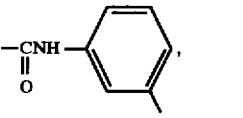
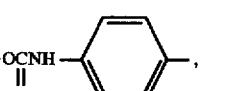
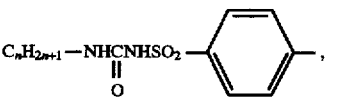
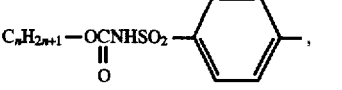
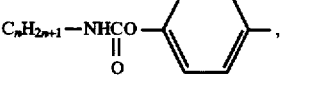
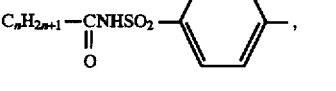
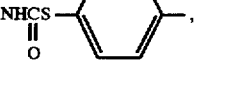
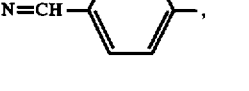

-continued

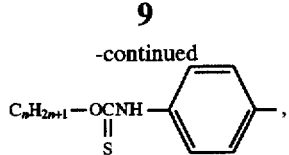

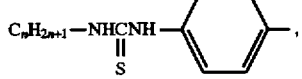

and

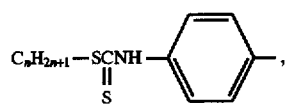

wherein n represents an integer of 11 or more, preferably to 30, still more preferably 14 to 21.

In the formulae (II) and (III), the divalent organic group represented by V is not limited to specific groups and is preferably selected from those of the formulae $-CH_2-$, $-CH_2CH_2CH_2-$, $-CH_2CH_2NHCH_2CH_2-$,

-continued

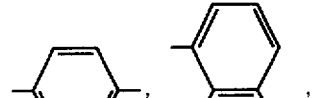

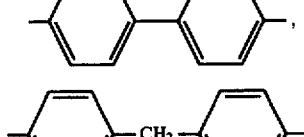

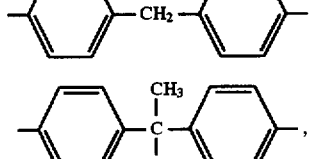

and

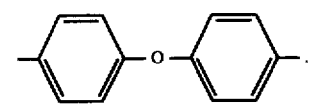

The color developing aromatic compounds of the formulae (II) and (III) usable for the thermosensitive reversible color-developing and disappearing agent, are preferably selected from the class consisting of the compounds of the formulae (IV) to (XXV):

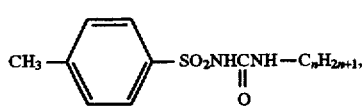 (IV)

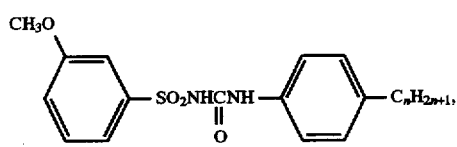 (V)

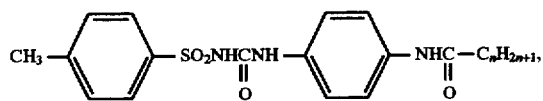 (VI)

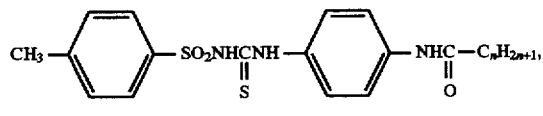 (VII)

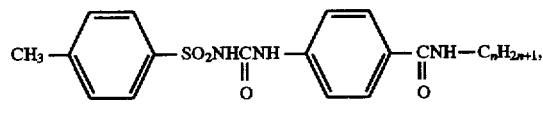 (VIII)

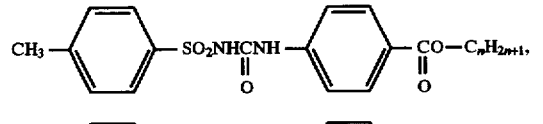 (IX)

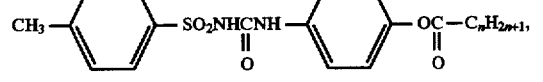 (X)

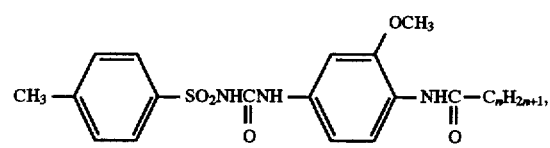
(XI)
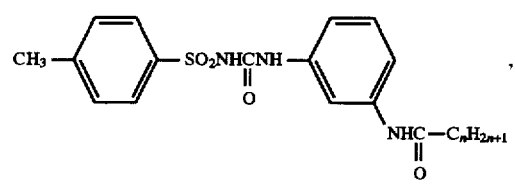
(XII)
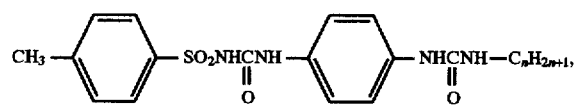
(XIII)
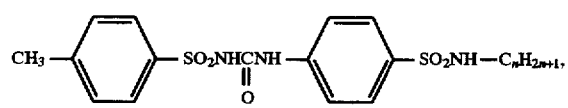
(XIV)
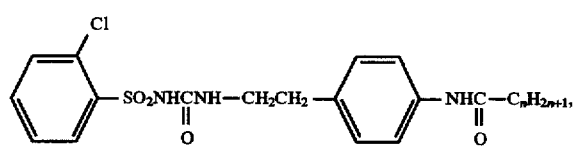
(XV)
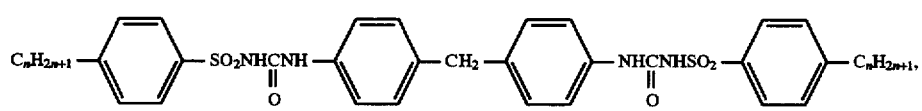
(XVI)
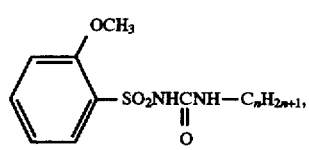
(XVII)
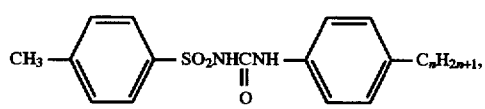
(XVIII)
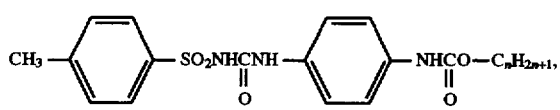
(XIX)
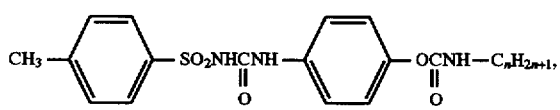
(XX)
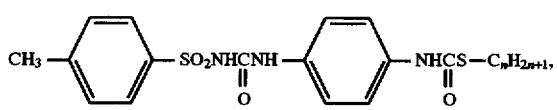
(XXI)
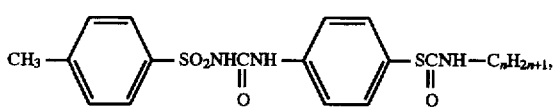
(XXII)
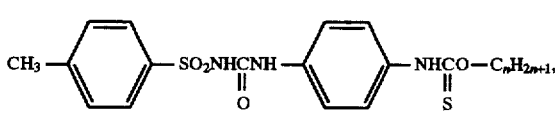
(XXIII)

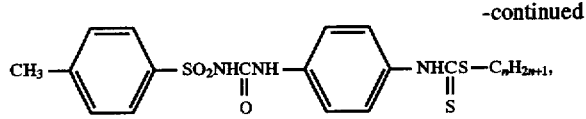

(XXIV)

and

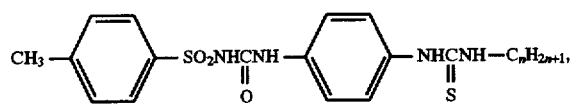

(XXV)

wherein n is as defined above.

Those aromatic compounds may be employed alone or in a mixture of two or more of the compounds.

As mentioned above, in the reversible color-developing and disappearing aromatic compound of the present invention, the long chain alkyl group preferably has 11 or more carbon atoms, more preferably 11 to 30 carbon atoms, still more preferably 14 to 21 carbon atoms. If the carbon atom number is less than 11, the resultant aromatic compound may exhibit an unsatisfactory color disappearing property. Also, if it is more than 30, the resultant aromatic compound may exhibit an unsatisfactory color-developing property.

The aromatic compounds of the formula (VI), namely N(p-toluenesulfonyl)-N'-[4-(n-alkanoylamino)phenyl]urea is very preferable for the present invention.

In the formula (VI), n is an integer of 11 or more, more preferably 17 to 21. The compounds of the formula (VI) are preferably selected from N-(p-toluenesulfonyl)-N'-[4-(n-octadecanoylamino)phenyl]urea, N(p-toluenesulfonyl)-N'-[4 -(n-eicosanoylamino)phenyl]urea, and N(p-toluenesulfonyl) -N'-[4-(n-docosanoylamino)phenyl]urea.

The aromatic compound of the formula (VI) can be prepared by the following reaction:

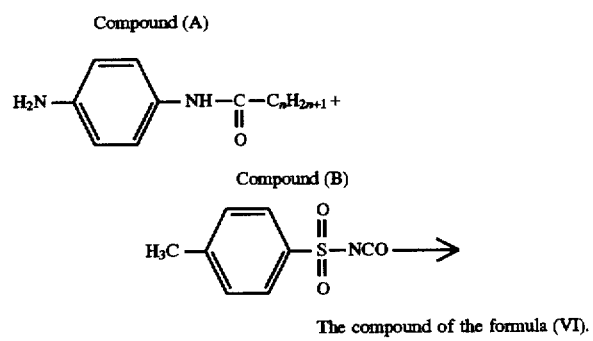

The compound of the formula (VI).

The compound (A) can be produced, for example, by reacting a corresponding long chain aliphatic carboxylic acid chloride with 4-nitroaniline, and reducing the nitro group of the resultant anilide compound into an amino group.

The reaction medium for the reaction of the compound (A) with the compound (B) (an isocyanate compound) is not limited to a specific solvent unless the solvent abstructs the reaction. Preferably the reaction medium comprises at least one compound selected from, for example, aliphatic halogenated hydrocarbons, for example, dichloromethane, chloroform, tetrachloromethane, and trichloroethylene; aliphatic nitrile compounds, for example, acetonitrile and propionitrile; aliphatic esters, for example, ethyl acetate, propyl acetate and butyl acetate; aliphatic ethers, for example, diethylether, dibutylether, and ethyleneglycoldimethylether; and aliphatic ketones, for example, 2-butanone and cyclohexanone.

In the reversible colored image-recording and disappearing material of the present invention, the thermosensitive colored image-forming layer comprises a substantially colorless dye precursor, a reversible color-developing and disappearing agent and a binder and, upon heating, a color is immediately developed by the reaction of the dye precursor with the reversible color-developing and disappearing agent, and the resultant colored images are maintained unchanged at room temperature. The colored images are made to disappear by heating to a temperature lower than the color-developing temperature, and the disappeared images are maintained at room temperature.

The reversible color-developing and disappearing mechanism is not completely clear at the present time. It is assumed that the (thio)urea group in the sulfonyl(thio) urea group of the formula (I) in the reversible color-developing and disappearing aromatic compound is activated by the sulfonyl group located adjacent to the (thio urea) group, and thus exhibits a strong color-developing activity to the basic dye precursor (leuco dye) and the dye-precursor is converted to a colored dye by heating the thermosensitive colored image-forming layer to a certain color-developing temperature. Also when the colored images are heated to a temperature lower than the color-developing temperature but higher than room temperature, the long chain alkyl group of the reversible color-developing and disappearing aromatic compound promotes the crystallization of the aromatic compound so as to separate the crystallized aromatic compound from the dye and thus the dye is converted to the colorless dye precursor and thus the color images are made to disappear.

Generally, the heating temperature for the color-development is 80° to 180° C. Also, the heating temperature for the color-disappearing is 50° to 120° and lower than the color developing temperature.

The color-development is effected usually by rapid heating using a thermal head in a printer, and the resultant colored images are fixed by rapidly cooling. The color-disappearing is effected by placing the colored images at a color-disappearing temperature range lower than the color-developing time for a certain time. The color-disappearing time is usually 0.5 second or more, for example, 0.5 to 60 seconds.

The color-developing and disappearing process will be explained in detail with reference to FIG. 1.

In FIG. 1, a non-recorded thermosensitive reversible colored image-recording and disappearing material held in condition A is heated in accordance with a desired pattern. The temperature of the recording material increases through condition B and reaches $T_2$. At a temperature $T_2$ or more, the color-developing reaction is advanced so that the color density of the colored images developed on the recording material rapidly increases through condition C. When the color-developing reaction is completed, the recording material reaches condition D in which the recorded colored images exhibit the highest color density. When the recording material in condition D is rapidly cooled to room temperature, the recording material reaches condition F through condition E. In condition F, the colored images on the recording material are maintained unchanged.

The color-developing process from condition A to condition F is completed through conditions B, C, D and E.

When the recording material held in condition F is heated to a temperature range $T_1$ through condition G and maintained at this temperature range for a certain time, the color density of the colored images gradually decreases. When the recording material reaches condition A', the colored images are made to completely disappear. The color-disappearing recording material is cooled to room temperature and reaches condition A. In condition A, the recording material is maintained in a colorless condition. The color-disappearing process from condition F to condition A is completed through condition G and condition A'.

The above-mentioned reversible color-developing and disappearing process can be repeatedly carried out.

In the thermosensitive colored image-forming layer of the thermosensitive reversible color-developing and disappearing record material of the present invention, the compounds usable as the dye precursor are selected from conventional triphenylmethane, fluoran and diphenylmethane leuco compounds. The dye precursor compounds include 3-(4-diethylamino-2-ethoxyphenyl)-3-(1-ethyl-2-methylindole-3-il)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(o,p-dimethyl-anilino) fluoran, 3-(N-ethyl-N-p-toluidino)-6-methyl-7-anilinofluoran, 3-pyrrolidino-6-methyl-7-anilinofluoran, 3-dibutyl-amino-6-methyl-7-anilinofluoran, 3-(N-cyclohexyl-N-methylamino)-6-methyl-7-anilinofluoran, 3-diethyl-amino-7-(o-chloroanilino)fluoran, 3-diethylamino-7-(m-trifluoromethylanilino) fluoran, 3-diethylamino-6-methyl-7-chlorofluoran, 3-diethylamino-6-methylfluoran, 3-cyclohexylamino-6-chlorofluoran and 3-(N-ethyl-N-hexylamino)-6-methyl-7-(p-chloroanilino) fluoran, and 3-dibutylamino-7-(o-chloroanilino) fluoran.

These dye precursory compounds may be employed alone or in a mixture of two or more thereof.

In the present invention, the thermosensitive colored image-forming layer optionally contains, in addition to the specific thermosensitive reversible color-developing and disappearing agent, a conventional color-developing agent comprising at least one member selected from, for example, phenolic compounds organic carboxylic acids and non-phenolic sulfonyl(thio) urea compounds having no long chain alkyl group, as long as the conventional color-developing agent does not obstruct the effect of the present invention.

The conventional color-developing agent may comprise at least one member selected from 2,2-bis(4-hydroxyphenyl) propane (bisphenol A), 1,1-bis(4-hydroxyphenyl)-1-phenylethane, 1,4-bis[1-methyl-1-(4'-hydroxyphenyl)ethyl] benzene, 1,3-bis[1-methyl-1-(4'-hydroxyphenyl)ethyl] benzene, dihydroxydiphenylether (Japanese Unexamined Patent Publication No. 1-180382), benzyl p-hydroxybenzoate (Japanese Unexamined Patent Publication No. 52-140483), bisphenol S, 4-hydroxy-4'-isopropoxydiphenylsulfone (Japanese Unexamined Patent Publication No. 60-13852), 1,1-di-(4-hydroxyphenyl)-cyclohexane, 1,7-di(4-hydroxyphenylthio)-3,5-dioxaheptane (Japanese Unexamined Patent Publication No. 59-52694), 3,3'-diallyl-4,4'-dihydroxydiphenyl-sulfone (Japanese Unexamined Patent Publication No. 60-208,286), N-(p-toluenesulfonyl)-N'-phenylurea, N-(p-toluenesulfonyl)-N'-p-methoxyphenyl) urea, N-(p-toluenesulfonyl)-N'-(o-tolyl)urea, N-(p-toluenesulfonyl)-N'-(m-tolyl)urea, N-(p-toluenesulfonyl)-N'-(p-tolyl)urea, N-(p-toluenesulfonyl)-N'-benzylurea (the above 6 compounds are disclosed in Japanese Unexamined Patent Publication (Kokai) No. 5-32,061), 4,4'-bis(p-toluenesulfonylaminocarbonylamino)-diphenylmethane, 4,4'-bis(o-toluenesulfonylaminocarbonylamino) diphenylmethane, 4,4'-bis (benzenesulfonylaminocarbonylamino)diphenylmethane, 1,2-bis[4'-(p-toluenesulfonylaminocarbonylamino) phenyloxy]ethane, 4,4'-bis(p-toluenesulfonylaminocarbonylamino)diphenylether, and 3,3'-bis(p-toluenesulfonylaminocarbonylamino) diphenylsulfone (the above 6 compounds are disclosed in Japanese Unexamined Patent Publication (Kokai) No. 5-147,357).

In the present invention, the thermosensitive colored image-forming layer optionally contains a heat-fusible substance, namely a sensitizing agent. The sensitizing agent comprises a heat-fusible organic compound having a melting temperature of 50° to 150° C. For example, the heat-fusible organic compound is selected from phenyl 1-hydroxy-2-naphthoate (Japanese Unexamined Patent Publication No. 57-191089), p-benzyl-biphenyl (Japanese Unexamined Patent Publication No. 60-82382), benzyl-naphthylether (Japanese Unexamined Patent Publication No. 58-87094), dibenzyl terephthalate (Japanese Unexamined Patent Publication No. 58-98285), benzyl p-benzyloxybenzoate (Japanese Unexamined Patent Publication No. 57-201691), diphenyl carbonate, ditolyl carbonate (Japanese Unexamined Patent Publication No. 58-136489), m-terphenyl (Japanese Unexamined Patent Publication No. 57-89994), 1,2-bis(m-tolyloxy)ethane (Japanese Unexamined Patent Publication No. 60-56588), 1,5-bi(p-methoxyphenoxy)-3-oxapentane (Japanese Examined Patent Publication No. 62-181183), oxalic acid diesters (Japanese Unexamined Patent Publication No. 64-1583) and 1,4-bis(p-tolyloxy) benzene (Japanese Unexamined Patent Publication No. 2-153783), di(4-methylbenzyl)oxalate (Japanese Examined Patent Publication No. 5-62,597), 1,2-di(3-methylphenoxy)ethane (Japanese Unexamined Patent Publication No. 60-56,588), diphenylsulfon (Japanese Examined Patent Publication No. 60-15,667), benzenesulfoanilide (Japanese Unexamined Patent 10 Publication No. 58-211,493), 2-chloroacetoacetanilide, 4-ethoxymethylsulfonylbenzene, 4-methoxyacetoacetanilide, o-methylacetanilide, 4-methoxybenzenesulfoanilide, 3,4-dimethylacetanilide, and 2-methoxybenzenesulfoanilide.

In the present invention, the thermosensitive colored image-forming layer contains a binder and optionally an additive, for example, wax and pigment.

The wax is preferably selected from paraffins, amide-based waxes, bisimide-based waxes, and metal salts of higher fatty acids.

The organic and inorganic pigments are preferably selected from inorganic fine particles of calcium carbonate, silica, zinc oxide, titanium dioxide, aluminum hydroxide, zinc hydroxide, barium sulfate, clay, anhydrous clay, talc, and surface-treated calcium carbonate and silica, etc. and organic fine particles of a urea-formaldehyde resin, styrene-methacrylate copolymer, polystyrene resin.

Also, for the aforementioned binder, use can be made of water-soluble polymeric materials, for example, various types of polyvinyl alcohols which have a different molecular weight from each other, starch and derivatives thereof, cellulose derivatives, for example, methoxy cellulose, carboxymethyl cellulose, methyl cellulose, ethyl cellulose, etc.; sodium polyacrylate, polyvinyl pyrrolidine, acrylic acid amide-acrylic acid ester copolymer, acrylic acid amine-acrylic acid ester-methacrylic acid terpolymer, alkali salt of styrene-maleic anhydride copolymer, polyacrylamide, sodium alginate, gelatine, casein, and so on; and latexes of polyvinyl acetate, polyurethane, styrene-butadiene copolymer, polyacrylic acid, polyacrylic acid ester, vinyl chloride-vinyl acetate copolymer, polybutyl methacrylate, ethylene-vinyl acetate copolymer, styrene-butadiene-acrylic terpolmer, etc.

In the thermosensitive colored image-forming layer of the thermosensitive reversible color-developing and disappearing record material of the present invention, preferably the dye precursor is contained in a content of 5 to 40% by weight, the reversible color-developing and disappearing agent is in a content of 5 to 50% by weight, based on the total dry weight of the thermosensitive colored image-forming layer. If the content of the reversible color-developing and disappearing agent is less than 5% by weight, the resultant thermosensitive colored image-forming layer may exhibit an unsatisfactory color-developing performance.

Also, if the content is more than 50% by weight, the color-developing performance may be saturated, the contrast between the color density in the color-developed condition and that in the color-disappearing condition may not be specifically enhanced, and thus an economical disadvantage may occur.

Where the thermosensitive colored image-forming layer contains the conventional color developing agent, for example, phenolic compounds, organic acids or non-phenolic sulfonyl(thio) urea compounds having no long chain alkyl group, the content of the conventional color-developing agent is preferably 10% by weight or less based on the total dry weight of the thermosensitive colored image-forming layer. If the content of the conventional color-developing agent is more than 10% by weight, the color-disappearing reaction may be obstructed thereby, and the contrast between the color-developed portion and the color-disappearing portion of the record material may be decreased.

Where the wax or white pigment is contained in the thermosensitive colored image-forming layer, the wax content is preferably 5 to 20% by weight and the white pigment content is preferably 10 to 50% by weight.

Also, the content of the binder is 5 to 20% by weight based on the total dry weight of the thermosensitive colored image-forming layer.

The substrate sheet usable for the thermosensitive reversible colored image-recording and disappearing material is selected from paper sheets, coated paper sheets produced by coating a pigment or latex on the surface thereof, laminate paper sheets, synthetic paper sheets produced from, for example, a polyolefin resin, plastic films, glass plates and electroconductive rubber sheets, which are usually used for the conventional thermosensitive colored image-recording sheets. On a surface of the substrate sheet, a coating liquid containing the necessary components is coated and dried to form a thermosensitive colored image-forming layer and to provide a thermosensitive reversible colored-image recording and disappearing material. The thermosensitive colored image-forming layer is preferably in preferably an amount of 1 to 15 g/m$^2$, more preferably 2 to 10 g/m2 on a dry basis.

In the thermosensitive reversible colored image-recording and disappearing material of the present invention, optionally, an additional coating layer, for example, a protect layer or printing layer is formed on the thermosensitive colored image-forming layer to enhance a resistance to heat, a printing performance, and a durability to repeated color-developing and disappearing procedures.

The colored image-recording (color-developing) procedure and the procedure for making colored images disappear (color-disappearing) can be carried out by using various means selected in view of purpose, for example, a thermal head, a constant temperature bath, a heating roller, a heating pen, or a surface heating element. The heating means are not limited to the above-mentioned heaters.

EXAMPLES

The present invention will be further explained by the following examples.

Synthesis Example 1

Preparation of N-(p-toluenesulfonyl)-N'-[4-(n-octadecanoylamino)phenyl]urea (Compound (VI)-(1))

The compound (VI)-(1) was prepared from a starting material consisting of 4-nitroaniline by a two step reaction method as follows.

In a three necked flask equipped with a dropping funnel, a thermometer and a reflux condenser, 138 g of p-nitroaniline was dissolved in a mixed solvent consisting of 200 ml of tetrahydrofuran and 140 ml of pyridine while passing nitrogen gas through the flask. Then, 333 g of octadecanoylchloride placed in the dropping funnel was gradually dropped into the flask over a time span of 20 minutes, while stirring the reaction mixture. After the completion of the dropping, the reaction mixture was further stirred for 2 hours. A solid reaction product was produced. The solid reaction product was collected by filtering, the filtrate was concentrated under a reduced pressure to produce crystals. The crystals were collected and recrystallized from ethyl alcohol. As a result, 364 g of 4'-nitro-n-octadecaneanilide was obtained at a yield of 90%.

The crystals were dissolved in 8000 ml of tetrahydrofuran, 95 g of a 5% palladium carbon was mixed into the solution. The reaction mixture was vigorously stirred in a hydrogen gas atmosphere under a pressure of 3 atmospheres for two hours. After the completion of the reaction, the palladium carbon was removed by filtering and then the solvent (tetrahydrofuran) was removed under reduced pressure to produce crystals. The resultant crystals were collected and recrystallized from ethyl alcohol. 4'-amino-n-octadecaneanilide was obtained in an amount of 300 g, at a yield of 89%.

The crystals were suspended in 6000 ml of toluene, and 174 g of p-toluenesulfonylisocyanate was gradually dropped into the suspension over the time of 10 minutes, while stirring the reaction mixture. After the completion of the dropping, the reaction mixture was further stirred for one hour while heating and refluxing. When the resultant reaction mixture was cooled to room temperature, white crystals were precipitated. The crystals were collected by filtering under reduced pressure, washed with acetonitrile and dried under reduced pressure. The target compound was obtained in an amount of 390 g at a yield of 85%.

The analysis results of the crystals were as follows.

$^1$H-NMR measurement results in ppm (measured in deuterated tetrahydrofuran)

$\delta$=0.90 (t, 3H), 1.29 (br. s, 28H), 1.58–1.75 (m, 2H), 2.24 (t, 2H), 2.40 (s, 3H), 7.33 (dd, 4H), 7.51 (d, 2H), 7.88 (d, 2H), 8.32 (s, 1H), 8.84 (s, 1H);

IR measurement results (KBr tablet method)

In this measurement, the following characteristic absorptions were confirmed.

3300, 2920, 2850, 1692, 1665, 1552, 1520, 1451, 1405, 1160 cm$^{-1}$.

Synthesis Example 2

Preparation of N-(p-toluenesulfonyl)-N'-[4-(n-eicosanoylamino)phenyl]urea (Compound (VI)-(2))

The compound (VI)-(2) was prepared from a starting material consisting of 4-nitroaniline by a two step reaction method as follows.

In a three necked flask equipped with a dropping funnel, a thermometer and a reflux condenser, 138 g of p-nitroaniline was dissolved in a mixed solvent consisting of 3000 ml of tetrahydrofuran and 140 ml of pyridine while passing nitrogen gas through the flask. Then, 364 g of eicosanoylchloride placed in the dropping funnel was gradually dropped into the flask over a time span of 20 minutes, while stirring the reaction mixture. After the completion of the dropping, the reaction mixture was further stirred for 2 hours. A solid reaction product was produced. The solid reaction product was collected by filtering, the filtrate was concentrated under a reduced pressure to produce crystals. The crystals were collected and recrystallized from ethyl alcohol. As a result, 355 g of 4'-nitro-n-eicosane anilide was obtained at a yield of 82%.

The crystals were dissolved in 10,000 ml of tetrahydrofuran, 87 g of a 5% palladium carbon was mixed into the solution. The reaction mixture was vigorously stirred in a hydrogen gas atmosphere under a pressure of 3 atmospheres for two hours. After the completion of the reaction, the palladium carbon was removed by filtering and then the solvent (tetrahydrofuran) was removed under reduced pressure to produce crystals. The resultant crystals were collected and recrystallized from toluene. 4'-amino-n-eicosaneanilide was obtained in an amount of 265 g, at a yield of 80%.

The crystals were suspended in 5000 ml of toluene, and 143 g of p-toluenesulfonylisocyanate was gradually dropped into the suspension over a time span of 10 minutes, while stirring the reaction mixture. After the completion of the dropping, the reaction mixture was further stirred for one hour while heating and refluxing. When the resultant reaction mixture was cooled to room temperature, white crystals were precipitated. The crystals were collected by filtering under reduced pressure, washed with acetonitrile and dried under reduced pressure. The target compound was obtained in an amount of 351 g at a yield of 89%.

The analysis results of the crystals were as follows.

'H-NMR measurement results in ppm (measured in deuterated tetrahydrofuran)

$\delta$=0.89 (t, 3H), 1.29 (br. s, 32H), 1.60–1.75 (m, 2H), 2.25 (t, 2H), 2.40 (s, 3H), 7.34 (t, 4H), 7.50 (d, 2H), 7.87 (d, 2H), 8.32 (s, 1H), 8.83 (s, 1H), 8.83 (s, IR measurement results (KBr tablet method)

3312, 2928, 2864, 1696, 1664, 1555, 1523, 1456, 1408, 1162 cm$^{-1}$.

Synthesis Example 3

Preparation of N-(p-toluenesulfonyl)-N'-[4-(n-docosanoylamino)phenyl]urea (Compound (VI)-(3))

The compound (VI)-(3) was prepared from a starting material consisting of 4-nitroaniline by a two step reaction method as follows.

In a three necked flask equipped with a dropping funnel, a thermometer and a reflux condenser, 138 g of p-nitroaniline was dissolved in a mixed solvent consisting of 3000 ml of tetrahydrofuran and 140 ml of pyridine while passing nitrogen gas through the flask. Then, 395 g of docosanoylchloride placed in the dropping funnel was gradually dropped into the flask over a time span of 20 minutes, while stirring the reaction mixture. After the completion of the dropping, the reaction mixture was further stirred for 2 hours. A solid reaction product was produced. The solid reaction product was collected by filtering, the filtrate was concentrated under a reduced pressure to produce crystals. The crystals were collected and recrystallized from ethyl alcohol. As a result, 405 g of 4'-nitro-n-docosaneanilide was obtained at a yield of 88%.

The crystals were dissolved in 12,000 ml of tetrahydrofuran, 92 g of a 5% palladium carbon was mixed into the solution. The reaction mixture was vigorously stirred in a hydrogen gas atmosphere under a pressure of 3 atmospheres for two hours. After the completion of the reaction, the palladium carbon was removed by filtering and then the solvent (tetrahydrofuran) was removed under reduced pressure to produce crystals. The resultant crystals were collected and recrystallized from toluene. 4'-amino-n-docosaneanilide was obtained in an amount of 322 g, at a yield of 85%.

The crystals were suspended in 6000 ml of toluene, and 162 g of p-toluenesulfonylisocyanate was gradually dropped into the suspension over the time of 10 minutes, while stirring the reaction mixture. After the completion of the dropping, the reaction mixture was further stirred for one hour while heating and refluxing. When the resultant reaction mixture was cooled to room temperature, white crystals were precipitated. The crystals were collected by filtering under reduced pressure, washed with acetonitrile and dried under reduced pressure. The target compound was obtained in an amount of 423 g at a yield of 90%.

The analysis results of the crystals were as follows.

'H-NMR measurement results in ppm (measured in deuterated tetrahydrofuran)

$\delta$=0.93 (t, 3H), 1.33 (br. s, 36H), 1.62–1.75 (m, 2H), 2.29 (t, 2H), 2.43 (s, 3H), 7.37 (dd, 4H), 7.54 (d, 2H), 7.90 (d, 2H), 8.36 (s, 1H), 8.89 (s, 1H);

IR measurement results (KBr tablet method) 3310, 2923, 2855, 1695, 1665, 1553, 1524, 1450, 1406, 1161 cm$^{-1}$.

Example 1

A thermosensitive reversible colored image-recording and disappearing sheet was prepared by the following procedures.

(1) Preparation of Aqueous Dye Precursor Dispersion A

| Component | Part by weight |
| --- | --- |
| 3-dibutylamino-6-methyl-7-anilinofluoran | 20 |
| 10% aqueous solution of polyvinyl alcohol | 10 |
| water | 70 |

The mixture was dispersed by using a sand grinder to an extent such that the resultant dispersed solid particle had an average size of 1 μm or less.

(2) Preparation of an Aqueous Color-Developing and Disappearing Agent Dispersion B

| Component | Part by weight |
|---|---|
| N-(p-toluenesulfonyl)-N'-[4'-n-octadecanoylamino)phenyl]urea (Formula (VI), n = 17) | 20 |
| 10% aqueous solution of polyvinyl alcohol | 10 |
| water | 70 |

The mixture was dispersed by using a sand grinder to an extent such that the resultant dispersed solid particles had an average size of 1 μm or less.

(3) Formation of Thermosensitive Colored Image-Forming Layer

A coating liquid was prepared by evenly mixing 50 parts by weight of the aqueous dispersion A and 200 parts by weight of the aqueous dispersion B with 30 parts by weight of a calcium carbonate pigment, 20 parts by weight of a 25% aqueous zinc stearate dispersion, 15 parts by weight of a 30% aqueous paraffin dispersion and 100 parts by weight of a 10% aqueous polyvinyl alcohol solution, and agitating the mixture.

A surface of a polyester film having a thickness of 75 μm was coated with the coating liquid and dried, to form a thermosensitive reversible colored image-recording and disappearing layer with a dry weight of 5.0 g/m².

(4) Super Calender Treatment

The sheet was treated by a super calender. The calendered surface of the resultant sheet had a Bekk smoothness of 3000 to 5000 seconds.

A thermosensitive reversible colored image-recording and disappearing sheet was obtained.

(5) Test (1)

(Color-developing test)

A specimen of the thermosensitive reversible colored image-recording and disappearing sheet was subjected to a color-developing test using a color-developing tester (Trademark: Tester THPMD made by Okura Denki K. K.) under a printing voltage of 21.7V at a printing pulse of 1.0 ms. The color density of the resultant colored images was measured by a Macbeth Reflection Color Density Tester RD-914 (trademark). The test result is shown in Table 1.

(6) Test (2)

(Colored image-retention test)

A specimen of the thermosensitive reversible colored image-recording and disappearing sheet was printed under the same conditions as in Test (1).

The colored image-formed sheet was stored in the ambient air atmosphere at a temperature of 40° C. for 7 days. Thereafter the color density of the colored images in the same manner as in Test (1).

The retention of the colored image was calculated in accordance with the following equation:

$$\text{Retention (\%) of colored images} = \frac{D_1}{D_0} \times 100$$

wherein $D_0$ represents a color density of the colored images before the retention test, and $D_1$ represents a color density of the colored image after the retention test.

The result is shown in Table 1.

(7) Test (3)

(Color-disappearing test)

A specimen of the thermosensitive reversible colored image-recording and disappearing sheet was printed in the same manner as in Test (1).

The printed specimen was heated in a thermal inclination tester (made by Toyo Seiki Seisakusho) at a temperature of 100° C. for 3 seconds. The color density of the heated colored images was measured in the same manner as in Test (1).

The result is shown in Table 1.

Example 2

A thermosensitive reversible colored image-recording and disappearing sheet was prepared and tested by the same procedures as in Example 1, except that in the preparation of the aqueous dispersion B, N-(p-toluenesulfonyl)-N'-[4'-(n-octadecanoylamino)phenyl]urea was replaced by N-(p-toluenesulfonyl)-N'-[4'-(n-eicosanoylamino)phenyl]urea (Formula (VI), n=19).

The test results are shown in Table 1.

Example 3

A thermosensitive reversible colored image-recording and disappearing sheet was prepared and tested by the same procedures as in Example 1, except that in the preparation of the aqueous dispersion B, N-(p-toluenesulfonyl)-N'-[4'-(n-octadecanoylamino)phenyl]urea was replaced by N-(p-toluenesulfonyl)-N'-[4'-(n-docosanoylamino)phenyl]urea (Formula (VI), n=21).

The test results are shown in Table 1.

In each of Examples 1 to 3, it was found that the color images could be repeatedly recorded and made to disappear on the thermosensitive colored image-forming layer. Therefore, it was confirmed that the thermosensitive reversible colored image-recording and disappearing sheets containing the specific aromatic compound of the formula (IV) - (1), (2) or (3) are suitable for repeated use.

Comparative Example 1

A thermosensitive reversible colored image-recording and disappearing sheet was prepared and tested by the same procedures as in Example 1, except that in the preparation of the aqueous dispersion B, N-(p-toluenesulfonyl)-N'-[4'-(n-octadecanoylamino)phenyl]urea was replaced by a salt of gallic acid with stearylamine.

The test results are shown in Table 1.

Comparative Example 2

A thermosensitive reversible colored image-recording and disappearing sheet was prepared and tested by the same procedures as in Example 1, except that in the preparation of the aqueous dispersion B, N-(p-toluenesulfonyl)-N'-[4'-(n-octadecanoylamino)phenyl]urea was replaced by 4'-hydroxy-n-octadecaneanilide. The test results are shown in Table 1.

TABLE 1

| Example No. | Test (1) Color density of developed colored images | Test (2) Colored image retention (%) | Test (3) Color density after disappearance |
|---|---|---|---|
| Example | | | |
| 1 | 1.42 | 88 | 0.16 |
| 2 | 1.34 | 89 | 0.14 |
| 3 | 1.29 | 91 | 0.13 |
| Comparative Example | | | |
| 1 | 0.51 | 55 | 0.21 |
| 2 | 0.90 | 38 | 0.21 |

Table 1 clearly shows that the aromatic compounds of the formula (VI)-(1), (2) and (3), effectively enable the colored images to be reversible recorded and to disappear on the recording sheet of the present invention. Also, the resultant colored images had a higher color density than those printed on the conventional dye-type thermosensitive reversible colored image-recording and disappearing sheets of Comparative Examples 1 and 2. Also, after the disappearing treatment is applied, the resultant colored images exhibited a very low color density. Therefore the contrast between the colored images before and after the disappearing procedure is applied is extremely high. Also, the colored images formed on the recording sheets of the present invention had a very high retention of 85% or more even after the storage in the air atmosphere at a temperature of 70° C. for 7 days.

Accordingly, the thermosensitive reversible colored image-recording and disappearing material of the present invention can be advantageously subjected to repeated practical use.

Example 4

A thermosensitive reversible colored image-recording and disappearing sheet was prepared by the following procedures.

(1) Preparation of Aqueous Dye Precursor dispersion A

| Component | Part by weight |
|---|---|
| 3-dibutylamino-7(o-chloro-anilino)fluoran | 20 |
| 10% aqueous solution of polyvinyl alcohol | 10 |
| water | 70 |

The mixture was dispersed by using a sand grinder to an extent such that the resultant dispersed solid particles had an average size of 1 μm or less.

(2) Preparation of an Aqueous Color-Developing and Disappearing Agent Dispersion B

| Component | Part by weight |
|---|---|
| N-(p-toluenesulfonyl)-N'-(n-tetradecanyl)urea (Formula (VI), n = 14) | 20 |
| 10% aqueous solution of polyvinyl alcohol | 10 |
| water | 70 |

The mixture was dispersed by using a sand grinder to an extent such that the resultant dispersed solid particles had an average size of 1 μm or less.

(3) Formation of a Thermosensitive Colored Image-Forming Layer

A coating liquid was prepared by evenly mixing 50 parts by weight of the aqueous dispersion A and 200 parts by weight of the aqueous dispersion B with 30 parts by weight of a calcium carbonate pigment, 20 parts by weight of a 25% aqueous zinc stearate dispersion, 15 parts by weight of a 30% aqueous paraffin dispersion and 100 parts by weight of a 10% aqueous polyvinyl alcohol solution, and agitating the mixture.

A surface of a polyester film having a thickness of 75 μm was coated with the coating liquid and dried, to form a thermosensitive reversible colored image-recording and disappearing layer with a dry weight of 5.0 g/m².

(4) Super Calender Treatment

The sheet was treated by a super calender. The calendered surface of the resultant sheet had a Bekk smoothness of 3000 to 5000 seconds.

A thermosensitive reversible colored image-recording and disappearing sheet was obtained.

(5) Color-Developing and Disappearing Test

A specimen of the thermosensitive reversible colored image-recording and disappearing sheet was subjected to a color-developing test using a color-developing tester (Trademark: Tester THPMD made by Okura Denki K. K.) under a printing voltage of 21.7V at a printing pulse of 1.0 ms. The color density of the resultant colored images was measured by a Macbeth Reflection Color Density Tester RD-914 (trademark).

The printed specimen was heated in a constant temperature bath at a temperature of 80° C. for 30 seconds. The color density of the heated colored images was measured by the Macbeth Reflection Color Density tester RD-914.

The test results are shown in Table 2.

Example 5

The same aqueous dispersions A and B as in Example 4 were prepared.

(1) Formation of a Thermosensitive Colored Image-Forming Layer

A coating liquid was prepared by evenly mixing 70 parts by weight of the aqueous dispersion A and 280 parts by weight of the aqueous dispersion B with 8 parts by weight of a calcium carbonate pigment, 20 parts by weight of a 25% aqueous zinc stearate dispersion and 170 parts by weight of a 10% aqueous polyvinyl alcohol solution, and agitating the mixture.

The coating solution was coated on a surface of a paper sheet having a basis weight of 50 g/m², and dried, to form a thermosensitive colored image-forming layer having a dry weight of 7.5 g/m².

(2) Formation of Overcoat Layer

A coating layer for an overcoat layer was prepared by mixing 5 parts by weight of an aqueous kaolinite dispersion (solid content: 60%), with 35 parts by weight of a 10% aqueous modified polyvinyl alcohol solution, 22 parts by weight of 10% aqueous casein solution, 1 part by weight of a 25% aqueous zinc stearate dispersion, 2 parts by weight of a dimethylurea cross-linking agent and 35 parts by weight of water.

The coating liquid was coated on the thermosensitive colored image-forming layer mentioned above, and dried to form a overcoat layer having a dry weight of 1.5 g/m².

The resultant coated sheet was treated by the super calender in the manner similar to in Example 4. The Bekk smoothness of the calendered surface was controlled to 800 to 1000 seconds.

A thermosensitive reversible colored image-recording and disappearing sheet was obtained.

A specimen of the resultant recording sheet was subjected to the same color-developing and disappearing test as in Example 4.

The test results are shown in Table 2.

Example 6

A thermosensitive reversible colored image-recording and disappearing sheet was prepared and tested by the same procedures as in Example 5, except that in the preparation of the aqueous dispersion (B), N-(p-toluenesulfonyl)-N'-(n-tetradecanyl)urea was replaced by N-(p-toluenesulfonyl)-N'-(n-undecanyl)urea (Formula (IV), n=11).

The test results are shown in Table 2.

Example 7

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(2-methoxybenzenesulfonyl)-N'-(n-tetradecanyl)urea (Formula (XVII), n=14).

The test results are shown in Table 2.

Example 8

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-(4'-n-nonadecylphenyl)urea (Formula (XVIII), n=19).

The test results are shown in Table 2.

Example 9

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-[4'-(n-tetradecanoylamino)phenyl]urea (Formula (VI), n=13).

The test results are shown in Table 2.

Example 10

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by 4,4'-bis(4-n-tetradecanylphenylsulfonyl-aminocarbonylamino) diphenylmethane (Formula (XVI), n=14).

The test results are shown in Table 2.

Example 11

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-[4'-(n-octadecanoyl)phenyl]urea (Formula (VI), n=17).

The test results are shown in Table 2.

Example 12

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-[4'-(n-eicosanoylamino)phenyl]urea (Formula (VI), n=19).

The test results are shown in Table 2.

Example 13

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-[4'-(n-docosanoylamino)phenyl]urea (Formula (VI), n=21).

The test results are shown in Table 2.

Example 14

A thermosensitive reversible colored image-recording and disappearing sheet was prepared and tested by the same procedures as in Example 5, except that in the preparation of the aqueous dispersion A, 3-dibutylamino-7-(o-chloroanilino)fluoran was replaced by 3-dibutylamino-6-methyl-7-anilinofluoran.

The test results are shown in Table 2.

Comparative Example 3

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by N-(p-toluenesulfonyl)-N'-(n-pentyl)urea.

The test results are shown in Table 2.

Comparative Example 4

A thermosensitive reversible colored image-recording and disappearing sheet was prepared and tested by the same procedures as in Example 5, except that in the preparation of

27 the aqueous dispersion B, N-(p-toluenesulfonyl)-N'-(n-tetradecanyl)urea was replaced by N-(2-p-toluenesulfonyl)-N'-(4-n-heptyl)urea.

The test results are shown in Table 2.

Comparative Example 5

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by 4,4'-bis(p-toluenesulfonylaminocarbonylamino)-diphenylmethane.

The test results are shown in Table 2.

Comparative Example 6

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by gallic acid.

The test results are shown in Table 2.

Comparative Example 7

A thermosensitive reversible colored image-recording and disappearing sheet was prepared and tested by the same procedures as in Example 5, except that in the preparation of the aqueous dispersion B, N-(p-toluenesulfonyl)-N'-(n-tetradecanyl)urea was replaced by ascorbic acid.

The test results are shown in Table 2.

Comparative Example 8

(1) Formation of Carbon Black Layer

A carbon black dispersion was prepared in the following composition.

| Component | Part by weight |
|---|---|
| Carbon black | 2 |
| 10% ethyl cellulose solution in ethyl alcohol | 98 |

The mixture was fully stirred to prepare a homogeneous dispersion for coating.

The coating dispersion was coated on a surface of a polyester film having a thickness of 75 μm and dried to form a carbon black layer having a dry weight of 3.0 g/m².

(2) Formation of Thermosensitive Layer

A coating liquid was prepared in the following composition.

| Component | Part by weight |
|---|---|
| Vinylidene chloride-acrylonitrile copolymer | 15 |
| behenic acid | 3 |
| Tetrahydrofuran | 82 |

The mixture was fully agitated to provide a homogeneous solution for coating.

The coating solution was coated on the carbon black layer mentioned above and dried to form a thermosensitive layer having a dry weight of 5.0 g/m²

28

A thermosensitive reversible colored image-recording and disappearing sheet was obtained.

The sheet was subjected to the same color-developing and disappearing test as in Example 5.

The test results are shown in Table 2.

TABLE 2

| | Item Color density | |
|---|---|---|
| Example No. | Before disappearing | After disappearing |
| Example | | |
| 4 | 1.30 | 0.12 |
| 5 | 1.28 | 0.12 |
| 6 | 1.35 | 0.15 |
| 7 | 1.34 | 0.14 |
| 8 | 1.29 | 0.11 |
| 9 | 1.31 | 0.12 |
| 10 | 1.29 | 0.13 |
| 11 | 1.39 | 0.16 |
| 12 | 1.37 | 0.15 |
| 13 | 1.30 | 0.14 |
| 14 | 1.37 | 0.17 |
| Comparative Example | | |
| 3 | 1.34 | 1.29(*) |
| 4 | 1.35 | 1.28(*) |
| 5 | 1.27 | 1.25(*) |
| 6 | 1.05 | 0.31 |
| 7 | 1.02 | 0.41 |
| 8 | 0.85 | 0.58 |

Note: (*)The colored images did not disappear

Table 2 clearly shows that in Examples 4 to 14, the colored images were formed in a satisfactory color density and could be satisfactorily disappeared. Namely, the contrast between the colored portion and the color-disappearing portion of the recording sheet is high.

In Comparative Examples 3 to 5, the colored images failed to disappear.

In Comparative Examples 6 to 8, the resultant colored images were not satisfactory in color density thereof, and the color-disappearing was also unsatisfactory.

In comparison of Examples 3 to 14 with Comparative Examples 3 to 5, it was confirmed that the long chain alkyl groups having 11 or more carbon atoms effectively enable the resultant color-developing sulfonyl(thio)urea compounds to exhibit a satisfactory color-disappearing performance without decreasing the color-developing performance of the compounds.

We claim:

1. A thermosensitive reversible color-developing and disappearing agent for a colored image-recording material, comprising at least one color-developing aromatic compound reactive with a substantially colorless dye precursor of the recording material to thereby develop color upon heating and make the color disappear upon heating to a temperature lower than the color-developing temperature, the color-developing aromatic compound having the formula (II):

$$Y-SO_2NHCNH-Z \quad\quad (II)$$
$$\overset{\|}{X}$$

wherein X represents a member selected from the class consisting of oxygen and sulfur atom, Y represents a member selected from the class consisting of unsubstituted aromatic cyclic groups, and substituted aromatic cyclic groups with at least one substituent selected from the class consisting of lower alkyl groups and lower alkoxy groups; Z represents a member selected from the class consisting of the groups of the formulae:

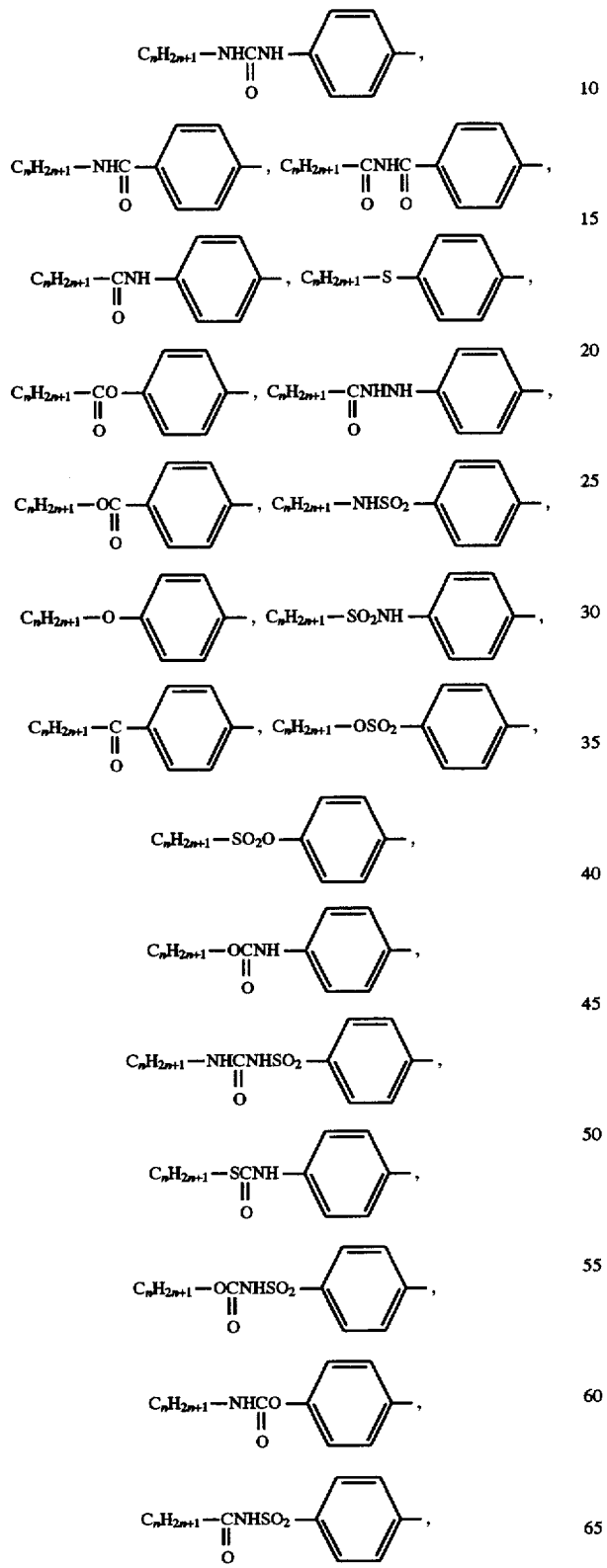

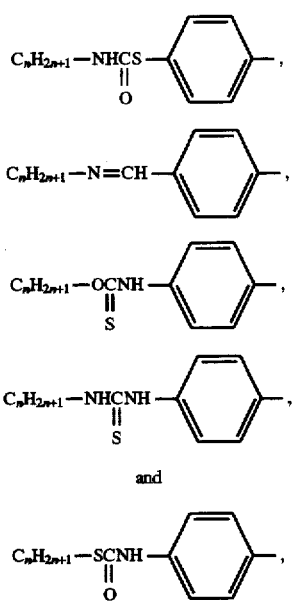

wherein n represents an integer of 11 or more.

2. The thermosensitive reversible color-developing and disappearing agent as claimed in claim 1, wherein in the formula (II), Y represents a member selected from the class consisting of the groups of the formulae:

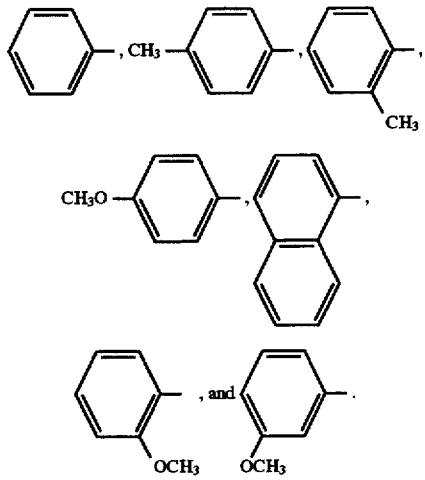

3. The thermosensitive reversible color-developing and disappearing agent as claimed in claim 1, wherein the color developing aromatic compound is selected from the class consisting of the compounds of the formulae:

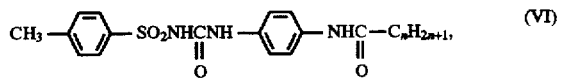 (VI)

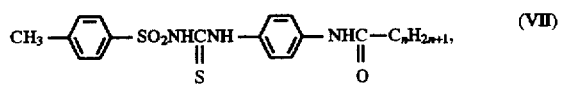 (VII)

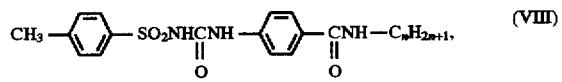 (VIII)

-continued $$CH_3-\langle\bigcirc\rangle-SO_2NHCNH-\langle\bigcirc\rangle-CO-C_nH_{2n+1},\quad (IX)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-OC-C_nH_{2n+1},\quad (X)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-NHCNH-C_nH_{2n+1},\quad (XIII)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-SO_2NH-C_nH_{2n+1},\quad (XIV)$$
$$\qquad\qquad\qquad\quad\;\;\overset{\|}{O}$$

$$CH_3-\langle\bigcirc\rangle-SO_2NHCNH-\langle\bigcirc\rangle-NHCO-C_nH_{2n+1},\quad (XIX)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-OCNH-C_nH_{2n+1},\quad (XX)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-NHCS-C_nH_{2n+1},\quad (XXI)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-SCNH-C_nH_{2n+1},\quad (XXII)$$
$$\qquad\qquad\qquad\quad\;\;\overset{\|}{O}\qquad\qquad\quad\;\overset{\|}{O}$$

$$CH_3-\langle\bigcirc\rangle-SO_2NHCNH-\langle\bigcirc\rangle-NHCO-C_nH_{2n+1},\quad (XXIII)$$
$$\qquad\qquad\qquad\quad\;\;\overset{\|}{O}\qquad\qquad\quad\;\overset{\|}{S}$$

$$CH_3-\langle\bigcirc\rangle-SO_2NHCNH-\langle\bigcirc\rangle-NHCS-C_nH_{2n+1},\quad (XXIV)$$
$$\qquad\qquad\qquad\quad\;\;\overset{\|}{O}\qquad\qquad\quad\;\overset{\|}{S}$$

and $$CH_3-\langle\bigcirc\rangle-SO_2NHCNH-\langle\bigcirc\rangle-NHCNH-C_nH_{2n+1},\quad (XXV)$$
$$\qquad\qquad\qquad\quad\;\;\overset{\|}{O}\qquad\qquad\quad\;\overset{\|}{S}$$

wherein n represents an integer of 11 or more.

4. The thermosensitive reversible color-developing and disappearing agent as claimed in claim 1, wherein the color-developing aromatic compound is selected from N-(p-toluenesulfonyl)-N'-[4'-(n-alkanoylamino)phenyl]ureas of the formula (VI):

$$H_3C-\langle\bigcirc\rangle-SO_2NHCNH-\langle\bigcirc\rangle-NHC-C_nH_{2n+1},\quad (VI)$$
$$\qquad\qquad\qquad\;\;\overset{\|}{O}\qquad\qquad\quad\;\overset{\|}{O}$$

wherein n represents an integer of 11 or more.

5. The thermosensitive reversible color-developing and disappearing agent as claimed in claim 4, wherein the compounds of the formula (VI) are selected from the class consisting of:

N-(p-toluenesulfonyl)-N'-[4'-(n-octadecanoylamino)phenyl]urea,

N-(p-toluenesulfonyl)-N'-[4'-(n-eicosanoylamino)phenyl]urea, and

N-(p-toluenesulfonyl)-N'-[4'-(n-docosanoylamino)phenyl]urea.

6. A thermosensitive reversible colored image-recording and disappearing material comprising a substrate sheet and a thermosensitive colored image forming layer formed on the substrate sheet and comprising a substantially colorless dye precursor and a reversible color developing and disappearing agent reactive with the dye precursor to thereby develop color upon heating and disappear the color upon heating at a temperature lower than the color-developing temperature, and a binder, the color developing agent comprising at least one color-developing aromatic compound being selected from the class consisting of the compounds of the formula (II):

$$Y-SO_2NHCNH-Z\quad (II)$$
$$\qquad\quad\;\;\overset{\|}{X}$$

wherein X represents a member selected from the class consisting of oxygen and sulfur atoms, Y represents a member selected from the class consisting of unsubstituted aromatic cyclic group, and substituted aromatic cyclic groups with at least one substituent selected from the class consisting of lower alkyl groups and lower alkoxy groups; Z represents a member selected from the class consisting of the groups of the formulae:

$$C_nH_{2n+1}-NHCNH-\langle\bigcirc\rangle-,$$
$$\qquad\qquad\;\;\overset{\|}{O}$$

$$C_nH_{2n+1}-NHC-\langle\bigcirc\rangle-,$$
$$\qquad\qquad\;\;\overset{\|}{O}$$

$$C_nH_{2n+1}-CNHC-\langle\bigcirc\rangle-,$$
$$\qquad\qquad\;\overset{\|}{O}\;\overset{\|}{O}$$

$$C_nH_{2n+1}-CNH-\langle\bigcirc\rangle-,$$
$$\qquad\qquad\;\overset{\|}{O}$$

$$C_nH_{2n+1}-S-\langle\bigcirc\rangle-,$$

$$C_nH_{2n+1}-CO-\langle\bigcirc\rangle-,$$
$$\qquad\qquad\;\overset{\|}{O}$$

$$C_nH_{2n+1}-CNHNH-\langle\bigcirc\rangle-,$$
$$\qquad\qquad\;\overset{\|}{O}$$

$$C_nH_{2n+1}-OC-\langle\bigcirc\rangle-,$$
$$\qquad\qquad\;\overset{\|}{O}$$

$$C_nH_{2n+1}-NHSO_2-\langle\bigcirc\rangle-,$$

$$C_nH_{2n+1}-O-\langle\bigcirc\rangle-,$$

-continued

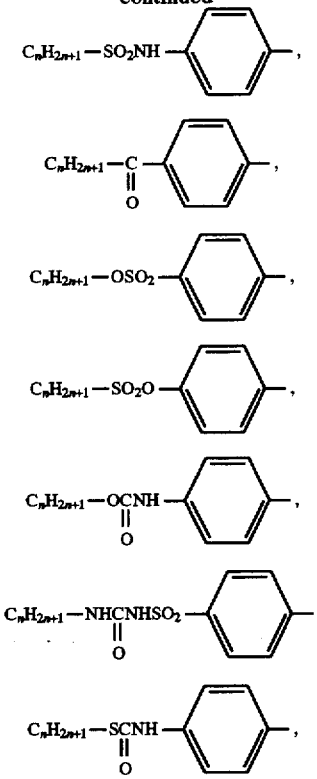

M

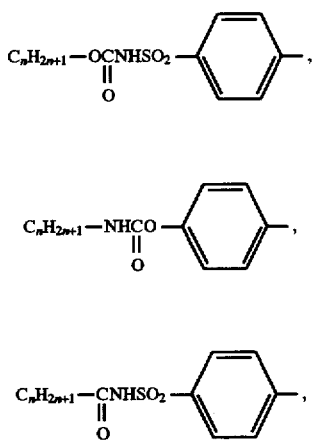

-continued

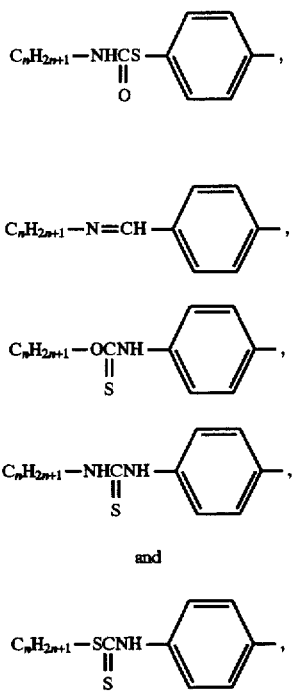

wherein n represents an integer of 11 or more.

7. A method of reversible recording and making disappear colored images on the thermosensitive reversible colored image-recording and disappearing material as claimed in claim 6, comprising the repeated steps of: heating image-wise the thermosensitive colored image-forming layer to record colored images on the colored image-forming layer; and after the recorded colored images become unnecessary, reheating the colored image-recorded layer to a temperature lower than the colored image-forming temperature and sufficient to make the colored images disappear.

* * * * *